United States Patent
Schrier et al.

[11] Patent Number: 5,888,495
[45] Date of Patent: Mar. 30, 1999

[54] METHOD OF PRODUCING STORAGE STABLE M-CSF LYOPHILIZATES

[75] Inventors: Jay A. Schrier, Peabody; Donald F. Williams, Somerville, both of Mass.

[73] Assignee: Genetics Institute, Inc., Cambridge, Mass.

[21] Appl. No.: 931,551

[22] Filed: Aug. 18, 1992

Related U.S. Application Data

[63] Continuation of Ser. No. 197,499, May 23, 1988, abandoned.

[51] Int. Cl.$^6$ ..................................................... A61K 37/02
[52] U.S. Cl. ................................ 424/851; 514/8; 514/12; 514/21; 530/351
[58] Field of Search ................................ 424/85.1; 514/8, 514/12, 21, 970, 975; 530/351

[56] References Cited

U.S. PATENT DOCUMENTS

| | | | |
|---|---|---|---|
| 4,847,201 | 7/1989 | Kaswasaki et al. | 435/252.3 |
| 4,929,700 | 5/1990 | Halenbeck et al. | 530/351 |
| 5,114,710 | 5/1992 | Jasaki | 424/85.1 |

FOREIGN PATENT DOCUMENTS

| | | |
|---|---|---|
| 249477 | 6/1987 | European Pat. Off. . |
| 0 284 249 | 3/1988 | European Pat. Off. . |
| WO8604587 | 8/1986 | WIPO . |
| WO8604607 | 8/1986 | WIPO . |
| WO8706954 | 11/1987 | WIPO . |

OTHER PUBLICATIONS

Remington's Pharmaceutical Sciences, Chapters 31 & 102 (pp. 589–602 & 1842–1858).
Dany et al *J Parental Sci and Tech* 1988 vol. 42, (25) pp. 53–526.
Wony et al, *Science* 235, 1987, pp. 1504–1509.
Lardner et al, *The EMBO Journal*, vol. 6(9) 1989, pp. 2693–2698.
Macheda et al, CA vol. 110, 1989, #219 071x.
Wang et al *J Parenteral Drug and Dosage,* 1980, vol. 34, pp. 452–462.
Wong et al., *Science,* 235: 1504–1508 (1987).
Kawasaki, et al., *Science,* 230: 291–196 (1985).
Yu–Chang et al., *J. Parenteal Science & Technology,* 42: S3–S26 (supp. 1988).
Yu–Change et al., *Review of Excipients and pH's for Parental Products Used in the United States,* J. Parenteral Drug Association, Vo. 34, No. 6 (Nov.–Dec. 1980) pp. 452–462.

*Primary Examiner*—Sally P. Teng
*Attorney, Agent, or Firm*—Steven R. Lazar

[57] ABSTRACT

Lyophilized M-CSF formulations are presented that are free of high molecular weight species and stable to prolonged storage.

6 Claims, No Drawings

METHOD OF PRODUCING STORAGE STABLE M-CSF LYOPHILIZATES

This application is a continuation of U.S. application Ser. No. 07/197,499 filed May 23, 1988, now abandoned.

Macrophage colony stimulating factor (M-CSF) is a regulatory glycoprotein that stimulates hematopoietic cell proliferation and differentiation. M-CSF has considerable therapeutic potential. For example, M-CSF may be used in activating mature white colls in cases of serious infection. M-CSF may also be used as a therapeutic agent for naturally occurring or radiation-induced leukopenia. Additionally, M-CSF may be used for killing tumor cells by coadministering it with certain antibodies directed to tumor-associated antigens as described in the commonly assigned, copending U.S. application Ser. No. 065,466, filed Jun. 23, 1987 now abandoned. M-CSF may also be administered to reduce cholesterol levels in the body.

Full-length M-CSF is described in Wong at al., Science, 235: 1504–1508 (1987). A cDNA sequence for human urinary M-CSF has been reported by E. S. Kawasaki et al., Science, 230: 291–196 (1985). Also see publications by E. R. Stanley. The production of full-length M-CSF by recombinant DNA techniques is described in PCT/US87/00835 (W087/06954). A truncated version is described in PCT/US86/00238 (W086/04607). Yet another version having deletions or substitutions in a transmembrane region is described in EP 249,477. It is contemplated that any of the above M-CSF polypeptides may be employed in the formulations of the present intention.

There is general agreement that the biologically active forms of the above proteins consist of two identical, heavily glycosylated subunits each having a complex quaternary structure. The production of homogeneous dimeric M-CSF is taught by Morris et al. (copending, commonly assigned U.S. application Ser. No. 187,802, filed 29 April, 1988 now abandoned), which also discloses that the integrity of the quaternary structure of the protein can be compromised by pH and solvent effects leading to the formation of aggregates and other high molecular weight species.

Applicants have discovered that lyophilization and subsequent storage of dimeric M-CSF may cause the formation and proliferation of two varieties of high molecular weight species. One such variety is non-covalently bound aggregates of dimers of M-CSF. Another such variety is aggregates which are covalently bound.

These non-covalent lyophilization-induced aggregates have been shown to possess virtually no biological activity by the Wong Mouse Bone Marrow Assay, which is described in Wong et al., Science, supra. Additionally, other aggregated forms of M-CSF that are covalently bound have been shown to have substantially higher immunogenicity than homogeneous dimeric M-CSF. See Morris et al., supra. This suggests that M-CSF aggregates may impart greater toxicity than the homogeneous dimeric M-CSF.

Further, it is widely appreciated that aggregation within protein solutions often leads to precipitation. Such precipitation is deleterious, leading to such recognized dangers as thrombosis, nonhomogeneity of dose, and clogged syringes.

Thus, safety and efficacy of pharmaceutical formulations of M-CSF are directly related to its stability. These concerns may be diminished by a homogeneous M-CSF formulation that is stable to lyophilization and subsequent prolonged storage.

THE INVENTION

The present invention provides storage stable lyophilized M-CSF formulations comprising about 0.1–2.0% of M-CSF, about 0.1–9% of a pharmaceutically acceptable polyoxyethylenic non-ionic surfactant, about 65–75% glycine, about 17–21% sucrose, and about 4–7% of a pharmaceutically acceptable buffering agent, said formulations upon reconstitution having a pH of about 6, and wherein protein analysis of said formulations exhibits only a single peak when assayed by gel filtration chromatography and a single molecular weight band by nonreducing SDS PAGE. All per cents are by weight unless otherwise specified.

These formulations maintain M-CSF as a storage stable homogeneous dimer free of M-CSF aggregates. The term "stable" refers to substantial retention of the level of biological activity as determined by the production of predominantly macrophage-containing colonies in the Wong Mouse Bone Marrow Assay described in Wong et al., Science, supra.

The presence of non-covalently bound M-CSF aggregates is indicated by a gel filtration peak extraneous to the dimeric M-CSF peak in the gel filtration procedure described in Morris et al., supra. The covalently bound aggregates are evidenced by a high molecular weight band on nonreducing SDS PAGE.

The preferred class of polyoxyethylenic non-ionic surfactants for use in the foregoing composition is the polysorbates. The preferred polysorbate is polysorbate 80. The preferred formulation has 0.005% polysorbate 80 prior to lyophilization. The poloxamers are another group of commercially available polyoxyethylenic non-ionic surfactants useful in this invention, particularly poloxamer 338. A preferred prelyophilized poloxamer formulation contains 0.05% of poloxamer 338.

The formulations of this invention further include glycine and sucrose, and are buffered to a pH of about 6 with a pharmaceutically acceptable buffering agent such as sodium citrate. An exemplary preferred prelyophilized formulation contains 0.5M glycine, 1% sucrose, and 10 mM sodium citrate.

The process of lyophilization is well known in the art. See Remington's Pharmaceutical Sciences, p.1538 (17th ed., 1985).

The formulations of this invention may be administered parenterally, e.g. intravenously, following reconstitution, preferrably with Water For Injection (WFI). When parenterally administered, the therapeutic compositions of this invention are non-pyrogenic, parenterally acceptable aqueous solutions.

EXAMPLE

Full-length M-CSF was produced in CHO cells in accordance with the method of Clark et al., PCT/US87/00835 (W087/06954). Homogeneous dimeric M-CSF was obtained in accordance with Morris et al., supra, hereby incorporated herein by reference.

A 200 ml. solution of 0.125 mg/ml M-CSF, 10 mM sodium citrate, 0.5M glycine, 1% sucrose, and 0.005% Polysorbate 80 at pH 6 was filtered through a 0.2 $\mu$m filter (Durapore) . The filtered solution, in two ml. aliquots, was dispensed into 100 ten ml. vials suitable for lyophilization. The vials were loaded into the lyophilizer and frozen at −40° C. for one hour. The condenser was chilled to −70° C., the product temperature was raised to −37° C. for ½ hour, and the chamber pressure was reduced to 50 mTorr. Pressure was maintained by a dry nitrogen bleed. The shelf temperature was raised such that the product temperature was raised to −35° C. to commence the primary drying. Primary drying was considered complete when the product temperature and the shelf temperature came into equilibrium. The shelf-surface temperature was then increased to +20° C. at a rate such that the shelf-surface temperature and product temperature differed by no more than 10° C. When the partial pressure of water vapor was less than 5 mTorr, the system was backfilled with dry nitrogen and the product vials were stoppered.

A representative lyophilized sample was reconstituted to 2 ml. with WFI and analyzed by gel filtration and nonreducing SDS PAGE. The gel filtration chromatogram showed a single peak and the SDS PAGE analysis showed a single molecular weight band at about 80 kD.

Numerous modifications may be made by one skilled in the art to the above formulations within the spirit of the present invention.

What is claimed is:

1. A method of producing a storage stable lyophilized M-CSF formulation capable (a) of being reconstituted with water for injection (WFI) and (b) of maintaining said M-CSF in a homogenous form, said formulation exhibiting both (1) a single peak when assayed by gel filtration chromatography and (2) a single molecular weight band by nonreducing SDS PAGE; said method comprising combining about 0.1–2.0% of M-CSF, about 0.1–9% of a pharmaceutically acceptable polyoxyethylenic non-ionic surfactant, about 65–75% glycine, about 17–21% sucrose and about 4–7% of a pharmaceutically acceptable buffering agent in a liquid solution, and lyophilizing said solution.

2. The formulation of claim 1 in which said surfactant is a polysorbate.

3. The formulation of claim 1 in which said surfactant is polysorbate 80.

4. The formulation of claim 1 in which said surfactant is a poloxamer.

5. The formulation of claim 1 in which said surfactant is poloxamer 338.

6. The method of claim 1, in which said M-CSF is full-length M-CSF.

* * * * *